(12) United States Patent
Schon

(10) Patent No.: US 11,029,268 B2
(45) Date of Patent: Jun. 8, 2021

(54) HYBRID NMR AND OCT SYSTEM

(71) Applicant: Clear-Cut Medical Ltd., Rehovot (IL)

(72) Inventor: Armin Schon, Nes Ziona (IL)

(73) Assignee: Clear-Cut Medical Ltd., Rehovot (IL)

( * ) Notice: Subject to any disclaimer, the term of this patent is extended or adjusted under 35 U.S.C. 154(b) by 0 days.

(21) Appl. No.: 16/636,709

(22) PCT Filed: Aug. 2, 2018

(86) PCT No.: PCT/IB2018/055803
§ 371 (c)(1),
(2) Date: Feb. 5, 2020

(87) PCT Pub. No.: WO2019/030620
PCT Pub. Date: Feb. 14, 2019

(65) Prior Publication Data
US 2020/0240936 A1    Jul. 30, 2020

Related U.S. Application Data

(60) Provisional application No. 62/541,727, filed on Aug. 6, 2017.

(51) Int. Cl.
*G01N 21/00* (2006.01)
*G01N 24/08* (2006.01)
(Continued)

(52) U.S. Cl.
CPC ........... *G01N 24/08* (2013.01); *A61B 5/0035* (2013.01); *A61B 5/055* (2013.01);
(Continued)

(58) Field of Classification Search
CPC ...... G01N 24/08; A61B 5/0035; A61B 5/055; G01B 9/02091; G01R 33/307;
(Continued)

(56) References Cited

U.S. PATENT DOCUMENTS

| 5,671,741 A | 9/1997 | Lang |
| 7,227,630 B1 | 6/2007 | Zavislan |

(Continued)

FOREIGN PATENT DOCUMENTS

| WO | 2008/127692 | 10/2008 |
| WO | 2017/060860 | 4/2017 |

OTHER PUBLICATIONS

PCT Search Report and Written Opinion PCT/IB2018/055803, dated Nov. 29, 2018.
(Continued)

*Primary Examiner* — Abdullahi Nur
(74) *Attorney, Agent, or Firm* — Dekel Patent Ltd.; David Klein

(57) ABSTRACT

A system includes an NMR system (10) including a coil (18) and a magnet (12) capable of obtaining NMR information from a tissue (17) and an MRI processor (19) for creating a pixel map of the tissue (17) from the NMR information. The system also includes an OCT system (20) with an OCT processor (21) capable of creating an optical coherence tomography of the tissue (17). A tissue sample holder (16) is coupled to a manipulator to move the tissue sample holder (16) to the NMR system (10) for creating the pixel map of the tissue (17) and to move the tissue sample holder (16) to the OCT system (20) for creating the optical coherence tomography of the tissue (17).

4 Claims, 1 Drawing Sheet

(51) Int. Cl.
| | |
|---|---|
| *A61B 5/00* | (2006.01) |
| *A61B 5/055* | (2006.01) |
| *G01B 9/02* | (2006.01) |
| *G01R 33/30* | (2006.01) |
| *G01R 33/48* | (2006.01) |
| *G01R 33/56* | (2006.01) |
| *G01R 33/563* | (2006.01) |

(52) U.S. Cl.
CPC ....... *G01B 9/02091* (2013.01); *G01R 33/307* (2013.01); *G01R 33/4808* (2013.01); *G01R 33/5601* (2013.01); *G01R 33/56341* (2013.01)

(58) Field of Classification Search
CPC ............ G01R 33/4808; G01R 33/5601; G01R 33/56341; G01R 33/448; G01R 33/465
See application file for complete search history.

(56) References Cited

U.S. PATENT DOCUMENTS

| | | | |
|---|---|---|---|
| 2012/0178076 A1* | 7/2012 | Fujita | G01R 33/28 435/1.2 |
| 2012/0314092 A1* | 12/2012 | Chu | G01N 15/1463 348/207.1 |
| 2017/0086675 A1 | 3/2017 | Li | |

OTHER PUBLICATIONS

"Rapid full-field OCT assessment of clinical tissue specimens (Conference Presentation)", Dalimier, Eugénie et al., Proceedings of the SPIE, vol. 9703, Mar. 7, 2016.

"Dual-modality photothermal optical coherence tomography and magnetic-resonance imaging of carbon nanotubes", Jason Tucker-Schwartz et al., Opt Lett., Optical Society of America, Mar. 1, 2012;37(5):872-4.

"Optical Coherence Tomography Grading Correlates with MRI T2 Mapping and Extracellular Matrix Content", David M. Bear et al., J Orthop Res. Apr. 2010 ; 28(4): 546-552.

"Concurrent multiscale imaging with magnetic resonance imaging and optical coherence tomography", Liang Chia-Pin, J Biomed Opt. Apr. 2013;18(4):046015.

\* cited by examiner

HYBRID NMR AND OCT SYSTEM

FIELD OF THE INVENTION

The present invention relates generally to a system and a method for ex-vivo imaging of tissue by both NMR (nuclear magnetic resonance) and OCT (optical coherence tomography) or other digital microscopy technologies.

BACKGROUND OF THE INVENTION

In minimally invasive processes tissue is either removed from an organ of a patient for further investigation (biopsy) or destroyed in a targeted manner (various ablation methods exist to destroy malignant tumors, among them cryo-ablation, RF ablation and laser ablation). However, in the prior art, there is no real-time feedback to the operator indicating whether the excised or destroyed tissue is cancerous or non-cancerous.

An example of excising tissue and checking for cancerous cells but not in real time is Mohs surgery for skin lesions. Mohs surgery is performed in four steps: a) surgical removal of a tissue specimen; b) mapping the tissue, freezing and cutting the tissue and then staining the tissue; c) examination and analysis of microscope slides in the pathology laboratory; and d) repeating the process until clean tissue is reached and possibly performing reconstructive surgery at the site of the excised tissue.

The procedure can take several hours because there is no real-time feedback to the surgeon indicating whether the excised or destroyed tissue is cancerous or non-cancerous.

As another example, pathological inspection of tissue removed during breast conserving surgery (BCS) can be achieved with a process called frozen section, by which the excised tissue is frozen to make it mechanically suitable for slicing. These slices are removed at several locations and inspected under a conventional light microscope. This process is labor intensive, requires a trained pathologist to be present during the surgery and achieves only sampling of the excised lump, not a complete inspection of the surface.

As another example, navigation with a bronchoscope down the bronchi in order to reach a specific location and remove suspicious tissue is very difficult with is no real-time feedback and may need to be repeated if there is doubt that tissue removed actually comes from the targeted location.

Another example is tumor ablation in which there is uncertainty with regard to the precise tumor boundary. There is a need for a reliable, real-time way to stop ablative processes at the margin between cancerous and healthy tissue.

SUMMARY OF THE INVENTION

The present invention seeks to provide improved systems and methods for ex-vivo inspection of tissue surgically removed, in a hybrid system that combines NMR and a microscopic technology, such as OCT, to produce both macroscopically complete inspection of the excised tissue and microscopic images from selected locations for detailed review and potentially diagnosis of diseases not distinguishable with NMR information alone, as is described more in detail below.

OCT can create cross-sectional images with resolutions in the 5-20 µm range and up to 2 mm depth penetration. However, using OCT by itself to investigate a macroscopic object like a lump of excised tissue with microscopic resolution is impractical or impossible to perform in real time because there is no hint of where to look, similar to searching for a needle in a hay stack. OCT would take a prohibitively long time to investigate the macroscopic object. Even if a future OCT system could scan a macroscopic lump in a reasonable time, this scan would produce thousands of very detailed images, which in turn would need to be reviewed by a trained pathologist in minutes.

MRI on the other hand offers fast inspection of the complete surface and generates easy to interpret images in the form of diffusion weighted parameter maps, but lacks the intrinsic contrast resolution to distinguish between different malignancies and other tissue irregularities.

MRI does require a dedicated z-axis gradient coil in order to deliver depth resolution allowing to assess the depth of an identified target tissue below the surface of the excised lump. Without that information, partial volume effects can make it difficult to distinguish between a medium T2* lesion at the surface, or a high T2* lesion below the surface.

However, in the present invention, combining OCT with MRI can solve all three problems.

Imaging using NMR can provide a pixel map of the surface of excised tissue, in which the color code of each pixel indicates the probability that the pixel contains malignant tissue (e.g., with DWI (Diffusion Weighted Imaging) the lower the diffusion coefficient the higher probability of malignant tissue). Based on the probability of where pathologically irregular or abnormal (e.g., cancerous) cells are located, the system can then use OCT to extract microscopic images from several locations in the suspicious pixels or lacations. These microscopic images are then analyzed to make a diagnosis based on the cellular microstructure of the tissue. Accordingly, the invention enables real-time imaging and analysis by reducing the procedure to a few cross sections only through suspicious pixels and looking for microstructure confirmative of malignancy. Additionally, the cross-sectional nature of the OCT images enables measuring the depth of a specific tissue below the surface of the excised lump and thus helps resolve partial volume effects present in MR surface maps.

Another advantage of the invention is that OCT works with a laser beam that can scan the tissue while the tissue is being held in the same tissue holder used for MRI (such as the CLEARPACK tissue holder, commercially available from ClearCut Medical Ltd., Israel). Thus, the NMR coils and magnets may be placed adjacent the OCT laser unit and the tissue holder may be moved from the NMR device to the OCT device and vice versa, while the tissue remains in the holder at all times. After an initial MR scan, the tissue holder may be moved to the OCT laser unit for scanning the pixels of interest (the tissue holder being transparent to the laser beam). The user may toggle between an overview map (from the NMR unit) and high resolution cross-sections (from the OCT unit).

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
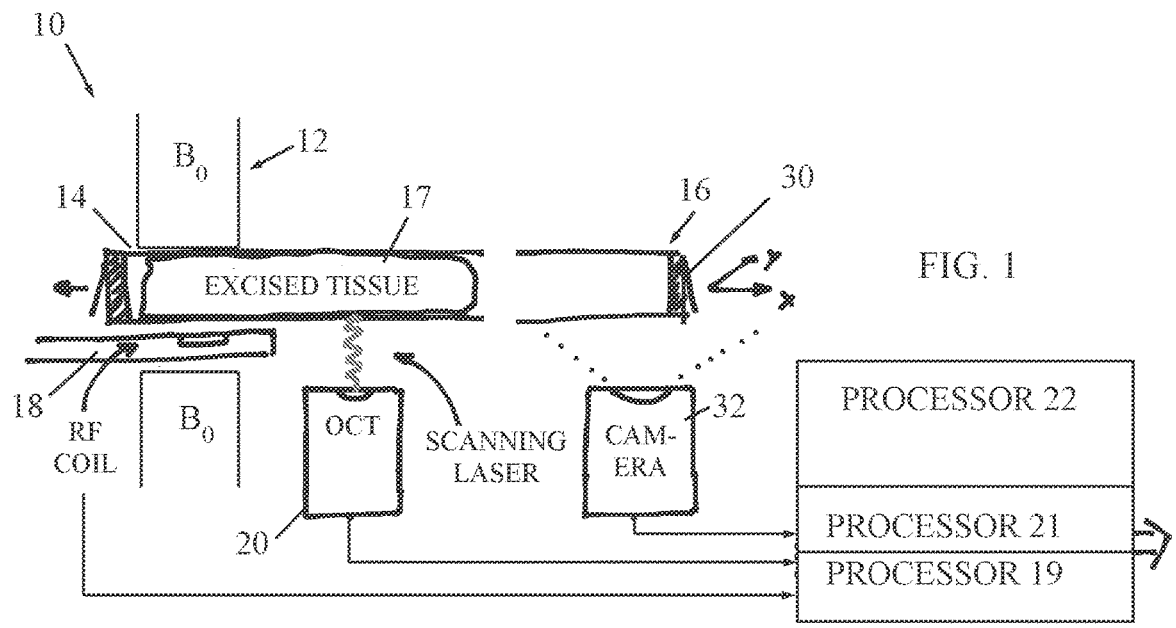
FIG. 1 is a simplified illustration of a hybrid system and method for ex-vivo NMR and OCT analysis of tissue removed either for purposes of biopsy or tissue removed during an ablation procedure, constructed and operative in accordance with a non-limiting embodiment of the present invention.

Reference is now made to FIG. 1, which illustrates a hybrid system and method for ex-vivo NMR and OCT analysis of tissue removed either for purposes of biopsy or tissue removed during an ablation procedure, constructed and operative in accordance with a non-limiting embodiment of the present invention.

The hybrid system includes an NMR system 10, also referred to as an MRI scanner 10. The MRI scanner 10 may include a magnet 12 (such as but not limited to, a permanent magnet, an electro-magnet, a super-conducting magnet, etc.) of any suitable shape and formed with a cavity or opening 14, into which a tissue sample holder 16 (in which a tissue 17 is received) may be inserted. The magnet 12 can be composed of one piece having a uniform magnetization direction, or of several pieces, each with a different magnetization direction, in order to optimize the static magnetic field ($B_0$) intensity and distribution (profile) within the region of the sample that needs to be measured/imaged. A transmit/receive (RF) coil 18 is mounted adjacent to opening 14, and is in close proximity to the outer surface of sample holder 16 with tissue 17 held therein. One or more gradient coils (not shown) may be positioned above and/or below the sample holder 16 with tissue 17. It is noted that the terms "upper", "lower", "above", "below", "left" and "right", and the like, only refer to the sense of the drawings and do not limit the invention in any way.

The magnet 12 produces a static magnetic field ($B_0$), which within the volume of tissue 17, is generally directed along the z-axis (vertical in the sense of the drawing). The transmit/receive coil 18, once activated, produces a time-varying RF ($B_1$) magnetic field perpendicular to the $B_0$ field, pointing towards the center of the tissue 17. The transmit/receive coil 18 can be designed to be large enough relative to the height of the ex-vivo tissue sample 17, so that the intensity of the $B_1$ field is relatively constant throughout the height of the sample. Although not mandatory, the transmit/receive coil 18 may be thin enough so as to effectively excite only nuclear spins that are located only within a relatively narrow and superficial sensitive region within the tissue sample 17, such as without limitation, from the surface of the sample up to a few millimeters into the sample. The depth of the sensitive region into the tissue sample 17 is determined by the coil sensitivity profile and by the homogeneity of the $B_0$ field, which can be sufficiently homogeneous if the sensitive region is up to a few millimeters into the sample. In order to obtain z-resolution, that is, to separate measurements originating at various z-positions within the sensitive region, upper and lower gradient coils can be used, so that when they are activated, they produce gradient ($B_G$) fields that are aligned along the +z and −z directions respectively. The gradient coils can create a $B_G$ field pattern that is linear in the z direction.

RF pulse sequences may be used in conjunction with the MRI scanner 10 to obtain a diffusion-weighted z-profile of the margins of the tissue sample 17. Diffusion weighted MRI can be a very sensitive and specific method to detect cancerous tissue. In one non-limiting example, a first (90°) RF pulse is followed by a second (180°) RF pulse with a time gap of τ. In between the two RF pulses, the z-gradient is activated ($B_{G1}$) for a short duration. After the second RF pulse, the same z-gradient is activated for a similar duration and amplitude. If the $B_0$ field is relatively homogenous within the sensitive region and if the spins do not diffuse, then at time 2×τ the spins should be completely refocused to create a gradient echo. The more self-diffusion the spins undergo, the more attenuated the gradient echo will be. In addition, if the z-gradient coil is active during signal acquisition (RF receive), then the gradient echo will contain z-position information. By applying a Fourier-transform to the acquired gradient echo, as is known in the art, a diffusion-weighted z-position vector is generated.

Another pulse sequence can be used in conjunction with the MRI scanner 10 to obtain a T2-weighted z-profile of the margins of tissue sample 17. Another pulse sequence can be used in conjunction with the MRI scanner 10, while using contrast enhancement agents to obtain a T2-weighted z-profile of the margins of tissue sample 17. In one non-limiting example, a first (90°) RF pulse is followed by a second (180°) RF pulse with a time gap of τ, which should be long enough relative to the typical T2 of the particular tissue. If the $B_0$ field is relatively homogenous within the sensitive region, then at time 2×τ the spins should be completely refocused to create a spin echo. The shorter the T2 is in the sensitive region, the more attenuated the gradient echo will be. In addition, if the z-gradient coil is active during signal acquisition (RF receive), then the spin echo will contain z-position information. By applying a Fourier-transform to the acquired gradient echo, as is known in the art, a T2-weighted z-position vector is generated. Similarly, T1-weighted, parametric ADC (apparent diffusion coefficient) measurement, or any other type of MRI pulse sequence known in the art, can be used in conjunction with the disclosed invention.

Much of the hardware and software of the existing CLEARSIGHT system (commercially available from ClearCut Medical Ltd., Israel) can be used to carry out the above described structure and methods of using MRI scanner 10. The system has an MRI processor 19 that processes the NMR information and displays images of the tissue, such as an image mapped with pixels.

The hybrid system also includes an OCT (optical coherence tomography) system 20. The basic hardware and software (OCT processor 21) of the existing VIVOSIGHT OCT system (commercially available from Michelson Diagnostics, UK) or other OCT systems can be used to carry out the invention.

In brief, OCT is based on low-coherence interferometry, in which interference of a broad-bandwidth light source occurs over a distance of micrometers. Non-limiting examples of broad-bandwidth light sources are superluminescent diodes or femtosecond lasers.

Light in the OCT system is broken into a sample arm (containing the item of interest) and a reference arm (usually a mirror). The combination of reflected light from the sample arm and reference light from the reference arm gives rise to an interference pattern, but only if light from both arms have traveled the "same" optical distance (that is, a difference of less than a coherence length). By scanning the mirror in the reference arm, a reflectivity profile of the sample can be obtained. This reflectivity profile, called an A-scan, contains information about the spatial dimensions and location of structures within the item of interest. A cross-sectional tomograph (B-scan) may be achieved by laterally combining a series of these axial depth scans (A-scan).

It is noted that OCT has been used as a modality for in-vivo imaging of skin cancer. For example, the article "Optical Coherence Tomography Used as a Modality to Delineate Basal Cell Carcinoma prior to Mohs Micrographic Surgery", Pomerantz et al., Case Rep Dermatol. 2011 September-December; 3(3): 212-218, describes using OCT as a modality for in vivo imaging of non-melanoma skin cancer (NMSC). As stated therein, by allowing identification of sub-surface margins of NMSC lesions, the use of OCT can improve the rate of complete excision and reduce the average number of stages during Mohs micrographic surgery (MMS). In that study, lesions were scanned with reference to a physical marker on the skin, and the apparent margins were then identified from the OCT images and marked on the skin. Photographs of these margins and the Mohs defect were correlated and compared. OCT appeared capable of visualizing the transition from lesional to normal tissue.

It is also noted that NMR has been used for detecting skin cancer but has not heretofore been used as a modality for real-time imaging of skin cancer.

For example, the article "NMR Metabolic Fingerprints Of Murine Melanocyte And Melanoma Cell Lines: Application To Biomarker Discovery", de Santana-Filho et al., Scientific Reports 2017, 7:42324, published online 15 Feb. 2017, describes using NMR to detect melanoma. As stated in the article, melanoma presents a major challenge in medical practice, due to difficulty in diagnosis, poor response to available therapies and high incidence in western populations. The study of melanoma has greatly benefited from the use of cell lines, which allow the investigation of progressive changes in the metabolism that correlate with the tumorigenic process. As a non-destructive technique, NMR can be used in the preliminary characterization of both water-soluble and lipid metabolites. This particular study applied NMR-based metabolomics strategies to characterize aqueous and lipid extracts from murine melanocytes and melanoma cell lines with distinct tumorigenic potential, successfully obtaining fingerprints of the metabolites from the extracts of the cell lines by means of 2D NMR HSQC (heteronuclear single quantum coherence) correlation maps. Relative amounts of the identified metabolites were compared between the 4 cell lines. Multivariate analysis of $^1$H NMR data was able not only to differentiate the melanocyte cell line from the tumorigenic ones but also distinguish among the 3 tumorigenic cell lines.

In the present invention, in contradistinction to the above-mentioned articles, the NMR system 10 may be used together with the OCT system 20 to provide microscopic images/information for analyzing the removed tissue in real time. The hybrid system may include a hybrid processor 22 that cooperates with the MRI processor 19 of NMR system 10 and the OCT processor 21 of the OCT system 20 and commands the processor 21 to have OCT system 20 scan those pixels which are considered suspicious of having cancerous cells by the processor 19 of NMR system 10.

Figure 2:
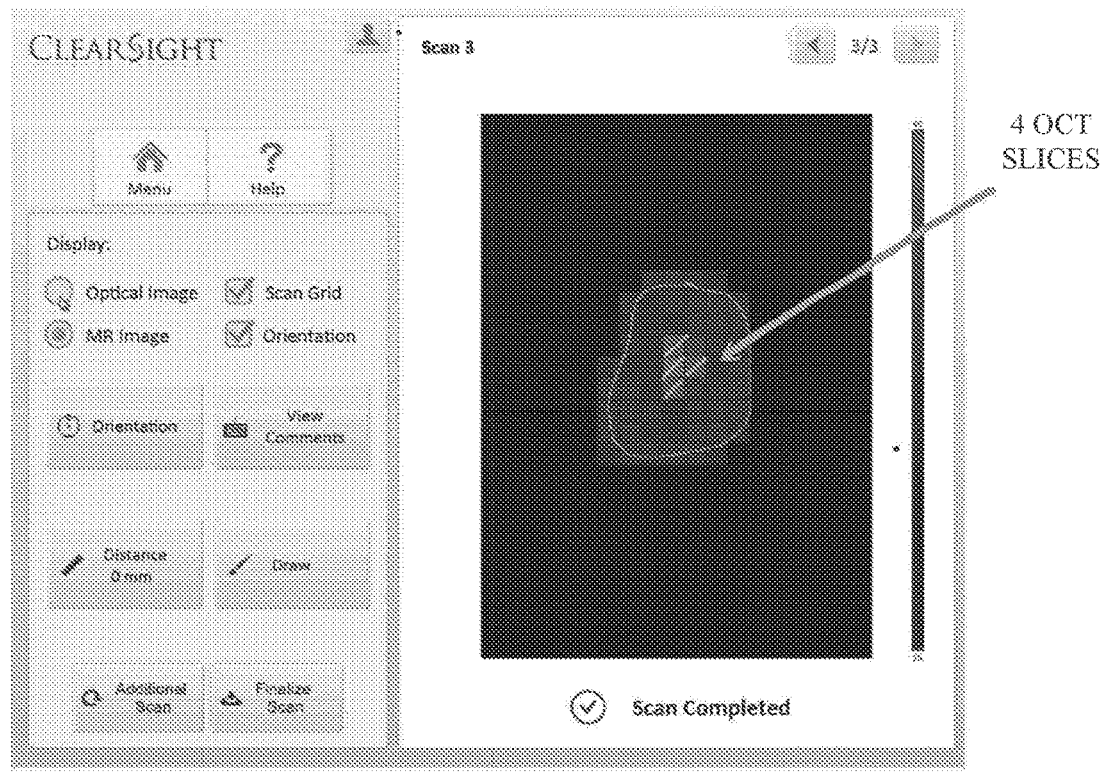
FIG. 2 is a simplified illustration of an OCT scan of a cross-section of tissue that had been marked as suspicious by an NMR system, in accordance with a non-limiting embodiment of the present invention.

The processor 19 of NMR system 10 produces a pixel map of the surface of excised tissue 17, in which the color code of each pixel indicates the probability that the pixel contains malignant tissue (e.g., the higher the T2* the higher that probability). Based on the probability of where cancerous cells are located, processor 22 commands the processor 21 of the OCT system 20 to use OCT to extract microscopic images from several locations in the suspicious pixels, as seen in FIG. 2. These microscopic images are then analyzed (either by the surgeon or by processor 22) to make a diagnosis based on the cellular microstructure of the tissue. Accordingly, the invention enables real-time imaging and analysis by reducing the procedure to a few cross sections only through suspicious pixels and looking for microstructure confirmative of malignancy.

The system of the invention may greatly reduce the time to perform Mohs micrographic surgery or other types of surgery and biopsy analysis, such as for breast cancer detection. It is particularly suited to perform real-time, surgical margin assessment during various cancer surgeries.

The tissue sample holder 16 may be moved on a manipulator 30 in any of three orthogonal directions, and may also be rotated. An example of a suitable tissue sample holder 16 is the CLEARPACK tissue holder, commercially available from ClearCut Medical Ltd., Israel. This tissue holder is constructed of MR inert materials and is transparent so it can easily be used with the OCT system 20. Manipulator 30 and/or a camera 32 may be in communication with processor 22. The camera 32 is used to generate a digital image of the tissue 17 inside the tissue sample holder 16, so the user can plan which sections of the tissue should be scanned. Correlation between MR map and photographic image may be done by toggling back and forth between the two images via the user interface or by way of synthetic overlay. The selected OCT scan positions can also be indicated on both the MR map and the photographic image.

Alternatively, the tissue and tissue holder may remain stationary, and manipulator 30 may be used to move the NMR system 10 and the OCT system 20 to the tissue and tissue holder to acquire the MR and optical coherence tomography information.

What is claimed is:

1. A system comprising:
    a nuclear magnetic resonance (NMR) system comprising a coil and a magnet capable of obtaining NMR information from a tissue and a magnetic resonance imaging (MRI) processor for creating a pixel map of said tissue from said NMR information;
    an optical coherence tomography (OCT) system comprising an OCT processor capable of creating an optical coherence tomography of the tissue;
    a tissue sample holder;
    a manipulator configured to cause relative movement between said tissue sample holder and said NMR system and said OCT system for creating the pixel map of said tissue and for creating the optical coherence tomography of the tissue; and
    a hybrid processor in communication with said MRI processor and said OCT processor, wherein said hybrid processor is configured to command said OCT processor to cause said OCT system to scan pixels considered suspicious of having pathologically irregular or abnormal cells by said MRI processor.

2. The system according to claim 1, further comprising a camera configured to generate an image of the tissue inside said tissue sample holder.

3. The system according to claim 1, wherein said NMR system uses T1 or T2 measurement, T1 or T2 measurements enhanced with contrast material, diffusion-weighted measurement, or a combination thereof.

4. A method for real-time tissue analysis comprising:
    using a nuclear magnetic resonance (NMR) system comprising a coil and a magnet capable of obtaining NMR information from a tissue and a magnetic resonance imaging (MRI) processor for creating a pixel map of said tissue from said NMR information; an optical coherence tomography (OCT) system comprising an OCT processor capable of creating an optical coherence tomography of the tissue; a tissue sample holder; and a manipulator configured to cause relative movement between said tissue sample holder and said NMR system and said OCT system for creating the pixel map of said tissue and for creating the optical coherence tomograph of the tissue;

and further comprising using said NMR system to create a pixel map of tissue from said NMR information, said pixel map having suspicious pixels considered suspicious of having pathologically irregular or abnormal cells by said MRI processor, and using said OCT system to scan said suspicious pixels and create an optical coherence tomography image of said suspicious pixels.

* * * * *